United States Patent [19]

Adachi et al.

[11] Patent Number: 4,978,681
[45] Date of Patent: * Dec. 18, 1990

[54] HAIR-GROWING AGENT

[75] Inventors: Kuniaki Adachi, Odawara; Hideo Tamai, Ninomiya; Masanao Sadai, Hiratsuka, all of Japan

[73] Assignee: Lion Corporation, Tokyo, Japan

[*] Notice: The portion of the term of this patent subsequent to Oct. 17, 2006 has been disclaimed.

[21] Appl. No.: 232,770

[22] Filed: Aug. 16, 1988

Related U.S. Application Data

[60] Division of Ser. No. 923,902, Oct. 28, 1986, Pat. No. 4,874,791, which is a continuation of Ser. No. 724,354, Apr. 18, 1985, abandoned, which is a continuation of Ser. No. 518,447, Jul. 29, 1983, abandoned.

[30] Foreign Application Priority Data

Aug. 10, 1982 [JP] Japan .................................. 57-137909

[51] Int. Cl.$^5$ ...................... A61K 31/19; A61K 31/20
[52] U.S. Cl. ...................................... 514/557; 514/558
[58] Field of Search ................................ 514/557, 558

[56] References Cited

U.S. PATENT DOCUMENTS 4,263,313 4/1981 Eckert et al. ........................ 514/558
4,745,103 5/1988 Oono et al. ......................... 514/558

FOREIGN PATENT DOCUMENTS 2477871 9/1981 France .
1469988 4/1977 United Kingdom .

OTHER PUBLICATIONS

Chemical Abstracts; vol. 106 (1987) #201540g; Oono et al.
Chemical Abstracts; vol. 102 (1985) #137579q; Adachi et al.
Chemical Abstracts; vol. 84 (1976) #35202d; Menyailo et al.

*Primary Examiner*—Joseph A. Lipovsky
*Attorney, Agent, or Firm*—Bacon & Thomas

[57] ABSTRACT

A hair-growing agent which exhibits a strong hair-growing effect. The hair-growing agent according to the present invention contains as an effective ingredient an aliphatic carboxylic acid having an odd number of carbon atoms or a derivative thereof.

10 Claims, No Drawings

HAIR-GROWING AGENT

This application is a division of application Ser. No. 923,902, filed Oct. 28, 1986 now U.S. Pat. No. 4,874,791; which is a continuation of Ser. No. 724,354, filed April 18, 1985, now abandoned, which is a continuation of Ser. No. 518,447, filed July 29, 1983, now abandoned.

BACKGROUND OF THE INVENTION

I. Field of the Invention

The present invention relates to a hair-growing agent.

II. Description of the Prior Art

Hair-growing agents containing various agents exhibiting pharmaceutical properties are known. Such pharmaceutical agents may include, for example, a vitamin such as vitamin E, an amino acid such as serine or methionine, a vasodilator such as an acetylcholine derivative, an anti-inflammatory agent such as lithospermum root extract, a female sex hormone such as estradiol, a skin function stimulant such as cepharanthine, a melanine synthesis catalyst such as copper pantothenate, a keratolytic such as salicylic acid, or the like. These agents may assist in the prevention and cure of alopecia.

There are known cases where an aliphatic carboxylic acid or a derivative thereof such as natural vegetable oil, e.g., olive oil and castor oil, or stearic acid is contained in a hair cosmetic such as a hair tonic or the like to improve performance of the product. Aliphatic carboxylic acids constituting various naturally occurring lipids, such as vegetable oils and animal oils, are in almost all cases aliphatic carboxylic acids having an even number of carbon atoms, whether they are saturated aliphatic carboxylic acids such as stearic acid and palmitic acid or unsaturated aliphatic carboxylic acids such as oleic acid and linoleic acid. There are no known cases where an aliphatic carboxylic acid having an odd number of carbon atoms or a derivative thereof is used in a hair cosmetic.

Conventional hair-growing agents are claimed to be effective in preventing or improving dandruff, itchiness and hair loss as well as in accelerating hair generation and growth. However, it seems that a satisfactory effect has not yet been obtained.

SUMMARY OF THE INVENTION

Therefore, the object of the present invention is to provide a hair-growing agent exhibiting a strong hair-growing effect.

The object can be accomplished by providing a hair-growing agent comprising as an effective ingredient an aliphatic carboxylic acid having an odd number of carbon atoms or a derivative thereof.

The hair-growing agent according to the present invention provides a strong hair-growing effect.

DETAILED DESCRIPTION OF THE PREFERRED EMBODIMENTS

Alopecia may arise from various causes. In each case, individual hairs cannot complete their normal hair cycle to reach the telogen state. In order to decrease baldness and accelerate hair generation, it is necessary to bring the hair follicles from the telogen state into the normal anagen state. As a result of extensive research into the conversion of hair from the telogen state into the anagen state, it has been found that an aliphatic carboxylic acid having an odd number of carbon atoms and a derivative thereof exhibit a remarkable hair-growing effect. The present invention is based on this finding.

The aliphatic carboxylic acid to be used for the hair-growing agent according to the present invention may be a saturated or unsaturated aliphatic carboxylic acid provided it has an odd number of carbon atoms. The unsaturated aliphatic carboxylic acid may contain a plurality of double bonds. The aliphatic carboxylic acid may be a lower aliphatic carboxylic acid such as propionic acid (having 3 carbon atoms) or valeric acid (having 5 carbon atoms), or a higher aliphatic carboxylic acid such as tricosanoic acid (having 23 carbon atoms) or pentacosanoic acid (having 25 carbon atoms). Preferred aliphatic carboxylic acids having an odd number of carbon atoms may include propionic acid, valeric acid, heptanoic acid, nonanoic acid, undecanoic acid, tridecanoic acid, pentadecanoic acid, heptadecanoic acid, nonadecanoic acid, heneicosanoic acid, tricosanoic acid and pentacosanoic acid.

For the hair-growing agent according to the present invention, any derivative of an aliphatic carboxylic acid having an odd number of carbon atoms as enumerated hereinabove may be used as an effective ingredient. However, needless to say, any compound which may adversely affect the human body cannot be used. Preferred derivatives include the following.

(A) a monoglyceride represented by the general formula (I) or (II):

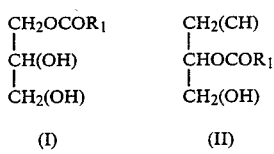

where $R_1$ is a straight-chain aliphatic group having an even number of carbon atoms.

(B) a diglyceride represented by the general formula (III) or (IV):

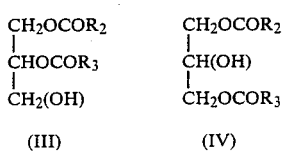

where at least one of $R_2$ and $R_3$ is a straight-chain aliphatic group having an even number of carbon atoms. It should be noted here that the effect to be accomplished by the present invention can be achieved if either $R_2$ or $R_3$ represents an aliphatic group having an even number of carbon atoms while the other represents a hydrogen or an aliphatic group having an odd number of carbon atoms or another organic group which does not adversely affect the human body. However, a diglyceride of an aliphatic carboxylic acid having an odd number of carbon atoms is particularly preferred.

(C) a triglyceride represented by the general formula (V):

where at least one of $R_4$, $R_5$ and $R_6$ is a straight-chain aliphatic group having an even number of carbon atoms. It should be noted here that, where at least one of $R_4$, $R_5$ and $R_6$ is a aliphatic group having an even number of carbon atoms, the effect sought by the present invention can be achieved even if the others are in each case hydrogen or an aliphatic group having an odd number of carbon atoms or another organic group which does not adversely affect the human body. However, a triglyceride of an aliphatic carboxylic acid having an odd number of carbon atoms is particularly preferred.

(D) an aliphatic carboxylic acid salt represented by the general formula (VI):

$$(R_7COO)_nM \qquad (VI)$$

where $R_7$ is a straight-chain aliphatic group having an even number of carbon atoms, M is a metal atom, and n is an integer corresponding the valence of M. Representatives may be $R_7COONa$, $R_7COOK$ and $R_7COOLi$.

(E) an ester represented by the general formula (VII):

$$R_8COOR_9 \qquad (VII)$$

where $R_8$ is a straight-chain aliphatic group having an even number of carbon atoms, $R_9$ is a residue of a primary or secondary alcohol, an amine residue, a polyoxyethylene residue, a sorbitan residue or a sucrose residue. A representative primary alcohol may be methanol and ethanol, and a representative amine residue is mono-, di- and tri-ethanolamine.

(F) a primary amide represented by the general formula (VIII):

$$R_{10}CONR_{11}R_{12} \qquad (VIII)$$

where $R_{10}$ is a straight-chain aliphatic group having an even number of carbon atoms, and $R_{11}$ and $R_{12}$ are independently a hydrogen atom or an organic group having no adverse effect on the human body.

(G) a secondary amide represented by the general formula (IX):

$$\begin{array}{c} R_{13}CONCOR_{14} \\ | \\ R_{15} \end{array} \qquad (IX)$$

where at least one of $R_{13}$ and $R_{14}$ is a straight-chain aliphatic group having an even number of carbon atoms, and $R_{15}$ may be a hydrogen atom or any organic group which does not adversely affect the human body. It should be noted here that where at least one of $R_{13}$ and $R_{14}$ is an aliphatic group having an even number of carbon atoms the effect of the present invention can be achieved, and that the other may be any organic group which does not adversely affect the human body although it is particularly preferred that both be a straight-chain aliphatic group having an even number of carbon atoms.

(H) a tertiary amide represented by the general formula (X):

$$\begin{array}{c} R_{16}CONCOR_{17} \\ | \\ COR_{18} \end{array} \qquad (X)$$

where at least one of $R_{16}$, $R_{17}$ and $R_{18}$ is a straightchain aliphatic group having an even number of carbon atoms. It is to be noted that where at least one of $R_{16}$, $R_{17}$ and $R_{18}$ is an organic group with an even number of carbon atoms, the present invention can achieve the desired effect, and also that the others may each be any organic group exerting no adverse influence on the human body. However, it is particularly preferred that all three be independently a straight-chain aliphatic group having an even number of carbon atoms.

(I) a dibasic carboxylic acid represented by the general formula (XI) or a salt thereof:

$$HOOCR_{19}COOH \qquad (XI)$$

where $R_{19}$ is a straight-chain aliphatic group having an odd number of carbon atoms.

(J) a sterol ester represented by the general formula (XII):

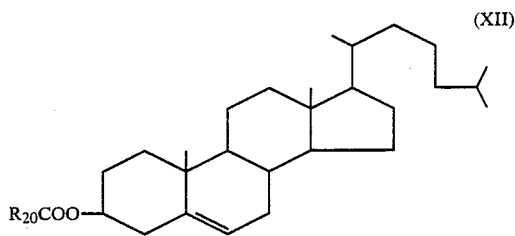

where $R_{20}$ is a straight-chain aliphatic group having an even number of carbon atoms.

(K) a phospholipid represented by the general formula (XIII):

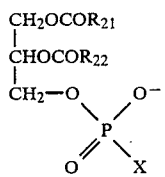

where at least one of $R_{21}$ and $R_{22}$ is an straight-chain aliphatic group having an even number of carbon atoms, and the other may be a hydrogen or an organic group having no adverse effect on the human body. However, it is preferred that both of $R_{21}$ and $R_{22}$ are independently a straight-chain aliphatic group having an even number of carbon atoms. X is a choline residue, an ethanolamine residue, a serine residue or an inositol residue. When X is a choline residue, it represents a phosphatidyl choline. When X is a ethanolamine residue, it represents a phosphatidyl ethanolamine. When X is a serine residue, it represents a phosphatidyl serine. When X is a inositol residue, it represents a phosphatidyl inositol.

(L) a phosphatidic acid represented by the general formula (XIV):

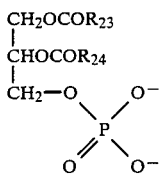

where at least one of $R_{23}$ and $R_{24}$ is an straight-chain aliphatic group having an even number of carbon atoms, and the other is a hydrogen or an organic group having no adverse effect on the human body. However, it is preferred that both of $R_{23}$ and $R_{24}$ are independently a straight-chain aliphatic group having an even number of carbon atoms.

(M) a sphingolipid represented by the general formula (XV):

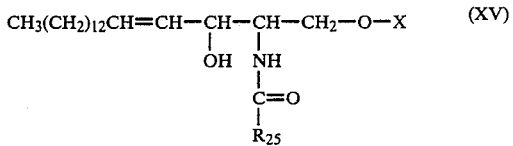

where $R_{25}$ is a straight-chain aliphatic group having an even number of carbon atoms, and X is a sugar residue, a phosphate residue or an amine base residue such as choline or ethanolamine.

The hair-growing agent according to the present invention may be used in a conventional manner in a variety of forms such as a hair-growing agent for an endermic liniment, a hair-growing agent for internal use, a hair-growing agent to be taken by injection, a hair tonic, hair lotion, hair cream, hair shampoo, hair rinse or the like.

In addition to the above-mentioned effective ingredients, the hair-growing agent according to the present invention may usually contain a cosmetically or pharmaceutically acceptable carrier. Such a carrier is not described in detail here since it is well known in this field. Examples of such a carrier include water; ethanol; a polyol such as ethylene glycol, propylene glycol, 1,3-butylene glycol, glycerine or sorbitol; a siloxane such as dimethyl polysiloxane, phenyl polysiloxane or polyoxyalkylene polysiloxane; an animal or vegetable oil such as sperm oil or jojoba oil; liquid paraffin; vaseline; paraffin wax; squalane; and an olefin oligomer.

The hair-growing agent according to the present invention may also contain an effective ingredient that is conventionally used. Such an effective ingredient may include, for example, a vitamin such as vitamin E, a hormone such as estradiol, a vasodilator such as an acetylcholine derivative, an amino acid such as serine or methionine, an anti-inflammatory agent such as lithospermum root extract, a skin function stimulant such as cepharanthine, or a keratolytic such as salicylic acid.

TEST 1: ANIMAL STUDY FOR EVALUATING EFFECTIVENESS

Aliphatic carboxylic acids having an odd number of carbon atoms and derivatives thereof were tested for their hair growing effects.

The tested substances were linear saturated aliphatic carboxylic acids having carbon atoms in variously odd and even numbers, and triglycerides of the aliphatic carboxylic acids. Test specimens were prepared by dissolving each test substance to be tested in ethanol. Concentrations of the test substance were 0.3, 3.0 and 10.0% by weight, respectively. As a control, ethanol containing no test substance was also tested.

The test animals were groups of 6 to 8 male rabbits of New Zealand White species each weighing about 2.5 kg from whose backs hair was removed. Rabbits in the telogen state alone were used. The test specimen was applied in the amount of 0.2 ml twice per week for 30 to 60 days to the area of the rabbits' backs from which the hair had been removed. The test was conducted by observing the number of days required for the conversion of hair from the telogen state into the anagen state. The results are shown in Table 1 below. In the Table, "shortened days" means the number of days by which the conversion of the telogen state into anagen state is shortened, compared with the control in which ethanol containing no test substance was applied. For example, when the number of shortened days is 10, it means that the conversion of telogen state into anagen state occurred 10 days earlier than the control experiment.

TABLE 1

| Test substance | Concentration (% by weight) | Hair-growing effect Shortened days | Overall evaluation |
| --- | --- | --- | --- |
| Propionic acid | 0.3 | 10 | Effective |
| Valeric acid | 0.3 | 12 | Effective |
| Heptanoic acid | 0.3 | 12 | Effective |
| Nonanoic acid | 0.3 | 14 | Effective |
| Hendecanoic acid | 0.3 | 18 | Effective |
| Tridecanoic acid | 0.3 | 20 | Effective |
| Pentadecanoic acid | 0.3 | 22 | Effective |
| Heptadecanoic acid | 0.3 | 22 | Effective |
| Nonadecanoic acid | 0.3 | 16 | Effective |
| Heneicosanoic acid | 0.3 | 12 | Effective |
| Tricosanoic acid | 0.3 | 12 | Effective |
| Pentacosanoic acid | 0.3 | 12 | Effective |
| Butyric acid | 0.3 | 2 | Ineffective |
| Caproic acid | 0.3 | 1 | Ineffective |
| Caprylic acid | 0.3 | 3 | Ineffective |
| Capric acid | 0.3 | 3 | Ineffective |
| Lauric acid | 0.3 | 1 | Ineffective |
| Myristic acid | 0.3 | 0 | Ineffective |
| Palmitic acid | 0.3 | 0 | Ineffective |
| Stearic acid | 0.3 | 0 | Ineffective |
| Arachic acid | 0.3 | 0 | Ineffective |
| Behenic acid | 0.3 | 0 | Ineffective |
| Lignoceric acid | 0.3 | 0 | Ineffective |
| Tripropionin | 3.0 | 10 | Effective |
| Tripentanoin | 3.0 | 16 | Effective |
| Triheptanoin | 3.0 | 20 | Effective |
| Trinonanoin | 3.0 | 22 | Effective |
| Trihendecanoin | 3.0 | 26 | Remarkably effective |
| Tritridecanoin | 3.0 | 28 | Remarkably effective |
| Tripentadecanoin | 3.0 | 30 | Remarkably effective |
| Triheptadecanoin | 3.0 | 30 | Remarkably effective |
| Trinonadecanoin | 3.0 | 22 | Effective |
| Triheneicosanoin | 3.0 | 18 | Effective |
| Tritricosanoin | 3.0 | 16 | Effective |
| Tributyrin | 3.0 | 2 | Ineffective |
| Tricaprone | 3.0 | 2 | Ineffective |
| Tricaprin | 3.0 | 4 | Ineffective |
| Tricaprylin | 3.0 | 2 | Ineffective |
| Trilaurin | 3.0 | 0 | Ineffective |
| Trimyristin | 3.0 | 0 | Ineffective |
| Tristearin | 3.0 | 0 | Ineffective |
| Triarachin | 3.0 | 0 | Ineffective |
| Tribehen | 3.0 | 0 | Ineffective |
| Trilignocerin | 3.0 | 0 | Ineffective |
| Tripropionin | 10.0 | 12 | Effective |
| Tripentanoin | 10.0 | 16 | Effective |
| Triheptanoin | 10.0 | 20 | Effective |
| Trinonanoin | 10.0 | 24 | Effective |
| Trihendecanoin | 10.0 | 28 | Remarkably effective |
| Tritridecanoin | 10.0 | 28 | Remarkably effective |
| Tripentadecanoin | 10.0 | 32 | Remarkably effective |
| Triheptadecanoin | 10.0 | 32 | Remarkably effective |
| Trinonadecanoin | 10.0 | 24 | Effective |
| Triheneicosanoin | 10.0 | 18 | Effective |
| Tritricosanoin | 10.0 | 18 | Effective |
| Tributyrin | 10.0 | 3 | Ineffective |
| Tricaprone | 10.0 | 2 | Ineffective |

TABLE 1-continued

| Test substance | Concentration (% by weight) | Hair-growing effect Shortened days | Overall evaluation |
|---|---|---|---|
| Tricaprin | 10.0 | 4 | Ineffective |
| Tricaprylin | 10.0 | 4 | Ineffective |
| Trilaurin | 10.0 | 2 | Ineffective |
| Trimyristin | 10.0 | 0 | Ineffective |
| Tripalmitin | 10.0 | 0 | Ineffective |
| Tristearin | 10.0 | 0 | Ineffective |
| Triarachin | 10.0 | 0 | Ineffective |
| Tribehen | 10.0 | 0 | Ineffective |
| Trilignocerin | 10.0 | 0 | Ineffective |

It can be seen from Table 1 that the aliphatic carboxylic acids having an odd number of carbon atoms and the glycerides thereof have significant hair-growing effects whereas the aliphatic carboxylic acids having even-numbered carbon chains as long as the former and the glycerides thereof have no hair-growing effect.

TEST 2: HUMAN STUDY FOR EVALUATING EFFECTIVENESS

A hair-growing composition comprising 10.0% by weight of n-trihendecanoin, 1.0% by weight of castor oil, 0.5% by weight of pyrrolidone carboxylic acid, 0.5% by weight of a perfume and 88% by eight of 80% ethanol was prepared. This composition was then used by patients (totaling 25 patients) suffering from various types of alopecia over a period of 3 to 6 months. The effects were evaluated according to subjective observation by the patients themselves. The results are shown in Table 2 below.

TABLE 2

| Alopecia | No. of cases | Results Remarkably Effective | Effective | Ineffective |
|---|---|---|---|---|
| Alopecia areata | 9 | 3 | 3 | 3 |
| Alopecia praematura and praesenilis | 10 | 3 | 4 | 3 |
| Alopecia furfuracea | 3 | 0 | 2 | 1 |
| Alopecia seborrheica | 3 | 1 | 0 | 2 |

It can be seen from Table 2 that the hair-growing agent according to the present invention is effective for various types of alopecia, particularly for male alopecia such as alopecia praematura and alopecia praesenilis as well as alopecia areata.

TEST 3: HUMAN STUDY FOR EVALUATING SAFETY

Pieces of gauze of 1 cm in diameter were soaked with the hair-growing composition prepared for Test 2. As a control, pieces of gauze of 1 cm in diameter were soaked with water.

Two pieces of each type of gauze (totaling 4 pieces) were attached as a closed patch by means of a fin chamber to the antebrachial flexor side of 25 healthy females for 24 hours. The skin conditions were observed after 30 minutes and 24 hours of the removal of the gauze. The result was that none of the women had any skin irritation.

The following indicates forms and compositions as examples of the hair-growing agents according to the present invention. In the following, the compositions are expressed in terms of % by weight.

EXAMPLE 1

Hair-Growing Composition for Endermic Liniment

| Ingredient | Amount |
|---|---|
| 80% ethanol | 88 |
| n-trihendecanoin | 10.0 |
| Castor oil | 1.0 |
| Pyrrolidone carboxylic acid | 0.5 |
| Perfume | 0.5 |

EXAMPLE 2

Hair-Growing Composition for Endermic Liniment

| Ingredient | Amount |
|---|---|
| 85% ethanol | 97.5 |
| n-nonanoic acid | 0.5 |
| Olive oil | 1.0 |
| α-tocopherol | 0.5 |
| Perfume | 0.5 |

EXAMPLE 3

Hair-Growing Composition for Endermic Liniment

| Ingredient | Amount |
|---|---|
| 90% ethanol | 92.5 |
| n-tritridecanoin | 5.0 |
| Olive oil | 1.0 |
| Glycyrrhizin | 1.0 |
| Perfume | 0.5 |

EXAMPLE 4

Hair-Growing Composition for Endermic Liniment

| Ingredient | Amount |
|---|---|
| 90% ethanol | 89.5 |
| Ethyl n-tridecanoate | 3.0 |
| Liquid paraffin | 5.0 |
| Polyethylene glycol | 2.0 |
| Perfume | 0.5 |

EXAMPLE 5

Shampoo Composition

| Ingredient | Amount |
|---|---|
| Lauryl ether sodium sulfate | 5.0 |
| α-olefin sodium sulfonate | 10.0 |
| Lauryl sulfate triethanol amine | 5.0 |
| n-tritridecanoin | 3.0 |
| Purified water | 77.0 |

EXAMPLE 6

Hair Rinse Composition

| Ingredient | Amount |
|---|---|
| Stearyl trimethyl ammonium chloride | 1.5 |
| Distearyl dimethyl ammonium | 0.5 |

-continued

| Ingredient | Amount |
| --- | --- |
| chloride | |
| Cetanol | 1.5 |
| Polyoxyethylene stearyl ether ($\bar{P} = 5$) | 2.0 |
| Liquid paraffin | 1.0 |
| Trihendecanoin | 3.0 |
| Purified water | 90.5 |

EXAMPLE 7

Hair Cream Composition

| Ingredient | Amount |
| --- | --- |
| n-tripentadecanoin | 10.0 |
| Olive oil | 5.0 |
| Liquid paraffin | 51.0 |
| Beeswax | 1.0 |
| Sorbitan sesquioleate | 3.0 |
| Purified water | 30.0 |

EXAMPLE 8

Hair Tonic Composition

| Ingredient | Amount |
| --- | --- |
| Ethyl n-nonanoate | 3.0 |
| Chillies tincture | 0.5 |
| Hinokitiol | 0.1 |
| α-tocopherol | 0.3 |
| Castor oil | 10.0 |
| Ethanol | 86.1 |

EXAMPLE 9

Hair-Growing Composition for Internal Use

| Ingredient | Amount |
| --- | --- |
| n-tripentadecanoin | 68.0 |
| Lactose | 20.0 |
| Corn starch | 10.0 |
| Magnesium stearate | 2.0 |

EXAMPLE 10

Hair-Growing Composition to be taken by Injection

| Ingredient | Amount |
| --- | --- |
| Tritridecanoin | 0.5 |
| Olive oil | 99.5 |

What is claimed is:

1. A method of stimulating growth of human hair on a human head suffering from or susceptible to alopecia which comprises bringing active human hair follicles on a human head from a telogen state into a normal anagen state by applying to said follicles a growth stimulating amount of an effective ingredient which is an aliphatic carboxylic acid which possesses an odd number of carbon atoms or a derivative thereof and is selected from the group consisting of n-propionic acid, n-valeric acid, n-heptanoic acid, n-nonanoic acid, a glyceride of said acids, a metal salt of said acids and mixtures thereof.

2. The method of claim 1 for treating makes with alopecia.

3. The method of claim 2 wherein the alopecia is alopecia areata.

4. The method of claim 2 wherein the alopecia is alopecia praematura or alopecia praesenilis.

5. The method of claim 2 wherein the alopecia is alopecia furfuracea.

6. The method of claim 2 wherein the alopecia is alopecia seborrheica.

7. The method of claim 2, wherein the effective ingredient is n-propionic acid, a glyceride or a metal salt thereof.

8. The method of claim 2, wherein the effective ingredient is n-valeric acid, a glyceride or a metal salt thereof.

9. The method of claim 2, wherein the effective ingredient is n-heptanoic acid, a glyceride or a metal salt thereof.

10. The method of claim 2, wherein the effective ingredient is n-nonanoic acid, a glyceride or a metal salt thereof.

* * * * *